United States Patent
Legrand

(10) Patent No.: US 7,803,355 B2
(45) Date of Patent: Sep. 28, 2010

(54) ANHYDROUS PASTE FOR BLEACHING HUMAN KERATIN FIBERS

(76) Inventor: Frédéric Legrand, 3 avenue du Chateau du Loir, Courbevoie 92400 (FR)

( * ) Notice: Subject to any disclaimer, the term of this patent is extended or adjusted under 35 U.S.C. 154(b) by 853 days.

(21) Appl. No.: 10/617,676

(22) Filed: Jul. 14, 2003

(65) Prior Publication Data

US 2004/0076594 A1    Apr. 22, 2004

Related U.S. Application Data

(60) Provisional application No. 60/402,942, filed on Aug. 14, 2002.

(30) Foreign Application Priority Data

Jul. 12, 2002    (FR) .................................. 02 08855

(51) Int. Cl.
*A61Q 5/08*    (2006.01)

(52) U.S. Cl. .................... 424/62; 424/70.11; 8/552; 132/202

(58) Field of Classification Search ........................ None
See application file for complete search history.

(56) References Cited

U.S. PATENT DOCUMENTS

| | | | |
|---|---|---|---|
| 5,437,860 A | 8/1995 | Jarvis et al. | |
| 5,578,299 A | 11/1996 | Starch | |
| 5,888,484 A | 3/1999 | Schmitt et al. | |
| 6,260,556 B1 * | 7/2001 | Legrand et al. | 132/208 |
| 6,365,136 B1 | 4/2002 | Lauscher et al. | |
| 6,423,306 B2 * | 7/2002 | Caes et al. | 424/78.02 |
| 6,540,791 B1 * | 4/2003 | Dias | 8/111 |

FOREIGN PATENT DOCUMENTS

| | | |
|---|---|---|
| EP | 0 808 895 | 11/1997 |
| EP | 1 066 827 A2 | 1/2001 |
| GB | 1 083 007 | 9/1967 |
| JP | A H08-175968 | 7/1996 |
| JP | A H11-012140 | 1/1999 |
| JP | A 2000-256150 | 9/2000 |
| JP | A 2001-039858 | 2/2001 |
| WO | WO 99/62469 | 12/1999 |

OTHER PUBLICATIONS

English Abstract of JP-A H11-012140 obtained from *esp@cenet* database.

* cited by examiner

*Primary Examiner*—Robert A Wax
*Assistant Examiner*—Hasan S Ahmed
(74) *Attorney, Agent, or Firm*—Finnegan, Henderson, Farabow, Garrett & Dunner LLP

(57) ABSTRACT

Disclosed herein is an anhydrous paste for bleaching human keratin fibers, such as hair, comprising at least one peroxygenated salt, at least one alkaline agent, from 15% to 35% by weight of at least one polydecene of formula $C_{10n}H_{[(20n)+2]}$ wherein n ranges from 3 to 9, such as from 3 to 7, relative to the total weight of the paste, and from 0.01% to 10% by weight of at least one gelling agent chosen from hydrophilic fumed silicas, hydrophobic fumed silicas and diblock, triblock, multiblock and radial-block copolymer comprising at least one segment of styrene monomers and at least one segment of monomers chosen from thermoplastic monomers and comonomers, relative to the total weight of the paste.

32 Claims, No Drawings

ANHYDROUS PASTE FOR BLEACHING HUMAN KERATIN FIBERS

This application claims benefit of U.S. Provisional Application No. 60/402,942, filed Aug. 14, 2002.

Disclosed herein is an anhydrous paste for bleaching human keratin fibers, such as hair, comprising at least one peroxygenated salt, at least one alkaline agent, from 15% to 35% by weight of at least one polydecene of formula $C_{10n}H_{[(20n)+2]}$ in which n ranges from 3 to 9, such as from 3 to 7, and from 0.01% to 10% by weight of at least one gelling agent chosen from hydrophilic fumed silicas, hydrophobic fumed silicas, and diblock, triblock, multiblock and radial-block copolymers comprising at least one segment of styrene monomers and at least one segment of monomers chosen from thermoplastic monomers and comonomers, wherein the weight percentages of the components are relative to the total weight of the paste.

Further disclosed herein is a process for bleaching human keratin fibers comprising applying to the human keratin fibers the paste described herein.

Human keratin fibers, such as the hair, can be bleached by oxidizing the "melanin" pigment therein, resulting in the dissolution and partial or total removal of this pigment.

To bleach the hair, bleaching powders containing a peroxygenated reagent such as one chosen from ammonium, alkali metal persulphates, perborates, and percarbonates can be used. The peroxygenated reagent can be combined at the time of use with an aqueous hydrogen peroxide composition.

Since peroxygenated salts and hydrogen peroxide are relatively stable in acidic medium, it may often be necessary to activate them at basic pH to obtain an adequate formation of oxygen. It is thus common practice to add to the bleaching powders alkaline compounds such as urea, alkali metal silicates and phosphates, such as alkali metal metasilicates, alkaline-earth metal silicates and phosphates, and ammonia precursors such as ammonium salts.

It is known that the bleaching powders can have a tendency to form dust during their handling, transportation and storage.

Given that the compounds of which the bleaching powders are composed (such as alkali metal persulphates and silicates) can be corrosive and irritant to the eyes, the respiratory pathways and mucous membranes, it has been proposed to reduce the level of dust by using various means, such as:

- by depositing on the powder, by means of a spraying process, various compounds that are substantially insoluble in water, such as oils and liquid waxes, which, by coating the powder particles, can aggregate them into particles of coarser size. For example, the patent EP 560 088 describes such a process;
- by using liquid anhydrous polymers that are soluble in water at room temperature, such as those chosen from polyethylene glycols and polypropylene glycols (French Patent No. 2 716 804), or block and/or random block linear polymers of the type such as polyoxyethylene/polyoxypropylene (patent EP 663 205); and
- by using, as in U.S. Pat. No. 5,866,107, compounds such as γ-butyrolactone, dimethyl isosorbide, diisopropyl isosorbide and $C_3$-$C_6$ dialkyl esters.

To overcome the problem of volatility of bleaching powders, pastes are now in development, which comprise the pulverulent agents (such as peroxygenated salts, alkaline agents, and thickeners) in a thickened organic inert liquid support. Such compositions are, for example, described in patent applications DE-3 814 356 A1 and DE-197 23 538 C1 and U.S. Pat. No. 4,170,637.

The bleaching pastes based on this technology that are currently available on the market comprise mineral oil as inert liquid. However, such compositions comprising mineral oil can give the hair a greasy feel after treatment.

They can also show unsatisfactory physicochemical stability and may not make it possible to obtain sufficiently uniform and powerful bleaching. Moreover, they may not have an attractive appearance.

To thicken the mineral oil and to improve the stability, waxes, such as products with a melting point of greater than 40° C., long-chain hydrophobic fatty acid esters, and beeswax substitution products have been used.

However, under these conditions, in order to be dispersed, or even dissolved, in the organic liquid, the wax should be molten, which may involve heating it during the manufacturing process. However, the present inventor has found that such wax-based compositions can be sensitive to temperature and to thermal shocks, both during their manufacture and their storage. The pastes can then lose their working qualities when they are exposed to large temperature variations or to extreme temperatures (less than or equal to 4° C. or greater than or equal to 45° C.).

Now, after considerable research conducted in this matter, the present inventor has discovered that by using at least one polydecene of formula $C_{10n}H_{[(20n)+2]}$ in which n ranges from 3 to 9, such as from 3 to 7, and at least one gelling agent chosen from hydrophilic fumed silicas, hydrophobic fumed silicas, and block polymers comprising at least one segment of styrene monomers and at least one segment of monomers chosen from thermoplastic monomers and comonomers—for example, the block polymers may contain at least one unit chosen from alkylene and alkylene oxide units—physicochemically stable anhydrous bleaching pastes could be obtained, which do not leave a greasy feel after bleaching.

Bleaching pastes can thus have the advantage of being prepared without being heated; they can be prepared under cold conditions or at room temperature and can be less sensitive to temperature and to thermal shocks during manufacture or storage.

Moreover, they can make it possible to obtain powerful and uniform bleaching, without leaving the hair greasy or coarse.

Disclosed herein is thus an anhydrous paste for bleaching human keratin fibers, such as the hair, comprising at least one peroxygenated salt, at least one alkaline agent, from 15% to 35% by weight of at least one polydecene of formula $C_{10n}H_{[(20n)+2]}$ in which n ranges from 3 to 9, such as from 3 to 7, and from 0.01% to 10% by weight of at least one gelling agent chosen from hydrophilic fumed silicas, hydrophobic fumed silicas, and diblock, triblock, multiblock and radial-block copolymers comprising at least one segment of styrene monomers and at least one segment of monomers chosen from thermoplastic monomers and comonomers, wherein the weight percentages of the components are relative to the total weight of the paste.

Further disclosed herein is the use of the anhydrous paste for the preparation of a ready-to-use bleaching composition.

As disclosed herein, the term "ready-to-use composition" means a composition intended to be applied, without modification, to the keratin fibers, i.e., it can be resulted, for example, from the extemporaneous mixing of the anhydrous paste disclosed herein and an aqueous hydrogen peroxide composition.

Further, as disclosed herein, the term "anhydrous" paste means a paste whose water content is less than 1% such as less than 0.5% by weight relative to the total weight of the paste.

Further disclosed herein is a process for bleaching human keratin fibers, such as the hair, comprising applying to the hair the ready-to-use bleaching composition as disclosed herein.

Even further disclosed herein is a multi-compartment device for the ready-to-use bleaching composition, comprising one compartment comprising at least one anhydrous paste and another compartment comprising at least one aqueous hydrogen peroxide composition.

Polydecenes of Formula $C_{10n}H_{[(20n)+2]}$ With n Ranging From 3 to 9

Polydecenes of formula $C_{10n}H_{[(20n)+2]}$ with n ranging from 3 to 9 correspond to the name "polydecene" in the CTFA Dictionary, 7th edition, 1997, of the Cosmetic, Toiletry and Fragrance Association, USA, and also to the same INCI name in the USA and in Europe.

They are products of hydrogenation of poly-1-decenes.

In one embodiment disclosed herein, n ranges from 3 to 7.

For example, the product sold under the name Silkflo® 366 NF Polydecene by the company Amoco Chemical, and those sold under the name Nexbasee® 2002 FG, 2004 FG, 2006 FG and 2008 FG by the company Fortum can be used.

In the bleaching paste disclosed herein, the at least one polydecene is present, for example, in an amount ranging from 15% to 30% by weight and such as from 15% to 25% by weight, relative to the total weight of the paste.

Gelling Agent

Among the hydrophilic fumed silicas that may be used herein, mention may be made, for example, of those sold by the company Degussa Hüls under the trade names Aerosile® 90, 130, 150, 200, 300 and 38.

Among the hydrophobic fumed silicas that may be used herein, mention may be made, for example, of those sold by the company Degussa Hüls under the trade name Aerosil® R202, R805, R812, R972 and R974.

The diblock, triblock, multiblock and radial-block copolymers comprising at least one segment of styrene monomers and at least one segment of monomers chosen from thermoplastic monomers and comonomers are described, for example, in U.S. Pat. No. 5,221,534.

Among these block copolymers, the monomers chosen from thermoplastic monomers and comonomers can be, for example, chosen from ethylene/$C_3$-$C_4$ alkylene and further, for example, chosen from hydrogenated copolymers comprising at least one styrene block and at least one block chosen from ethylene/$C_3$-$C_4$ alkylene blocks.

A mixture of at least one hydrogenated copolymer comprising at least one butylene/ethylene block and at least one styrene block and of at least one hydrogenated copolymer comprising at least one ethylene/propylene block and at least one styrene block, in mineral oil, such as from 1% to 20% by weight of the mixture of the at least one hydrogenated copolymer comprising at least one butylene/ethylene block and at least one styrene block and of at least one hydrogenated copolymer comprising at least one ethylene/propylene block and at least one styrene block in from 80% to 99% by weight of mineral oil, can be used.

Such mixtures are sold, for example, by the company Penreco under the trade names Versagele® M200 and Geahlenee® 200 and Versagele® M750 and Geahlene® 750, or by the company Aiglon under the trade names Transgel® or Syngel® (90% liquid paraffin, 5% hydrogenated butylene/ethylene/styrene copolymer, 5% hydrogenated ethylene/propylene/styrene copolymer).

It is also possible to use the styrene/ethylene-butylene/styrene triblock polymers (INCI name "Hydrogenated styrene/butadiene copolymer") sold by the company Shell Chimie under the trade names Kratone® G-1650, G-1652 and G-1657.

In the paste disclosed herein, the at least one gelling agent is, for example, present in a concentration ranging from 0.01% to 10%, such as from 0.01% to 5% and further such as from 0.1% to 2.5% by weight, relative to the total weight of the paste.

Peroxygenated Salts

As discussed above, the at least one peroxygenated salt can be chosen, for example, from ammonium and alkali metal persulphates, perborates and percarbonates, and magnesium peroxide.

Persulphates can, for example, be used; and, among these, sodium and potassium persulphates can, for example, be used.

In the bleaching paste disclosed herein, the at least one peroxygenated salt may be present in a concentration ranging from 10% to 70% and such as from 20% to 60% by weight, relative to the total weight of the paste.

Alkaline Agents

The at least one alkaline agent already described above, chosen, for example, from urea, alkali metal silicates and phosphates, such as alkali metal metasilicates, alkaline-earth metal silicates and phosphates, and ammonia precursors such as ammonium salts, may be present in the bleaching paste in a concentration ranging from 0.01% to 40% and such as from 0.1% to 30% by weight, relative to the total weight of the paste.

According to one alternative, the at least one alkaline agent may be present in an aqueous composition to be mixed at the time of use with the aqueous hydrogen peroxide composition.

Further disclosed herein is an anhydrous paste for bleaching human keratin fibers, such as the hair, comprising from 10% to 70% by weight of at least one peroxygenated salt chosen from sodium and potassium persulphates, from 0.01% to 40% by weight of at least one alkaline agent, from 5% to 35% by weight of at least one polydecene of formula $C_{10n}H_{[(20n)+2]}$ in which n ranges from 3 to 9, such as from 3 to 7, and from 0.01% to 10% by weight of at least one gelling agent chosen from hydrophilic fumed silicas, hydrophobic fumed silicas, and hydrogenated block copolymers comprising at least one styrene block and at least one block chosen from $C_3$-$C_4$ ethylene/alkylene blocks. The weight percentages of the components are relative to the total weight of the paste.

In one embodiment, the paste disclosed herein further comprises at least one amphiphilic polymer comprising at least one fatty chain chosen from nonionic and anionic fatty chains.

The at least one amphiphilic polymer can be chosen from, for example:

Nonionic Amphiphilic Polymers Comprising at Least One Fatty Chain

Nonionic amphiphilic polymers comprising at least one fatty chain are, for example, chosen from:

(1) celluloses modified with at least one group comprising at least one fatty chain; mention may be made, for example, of:

hydroxyethylcelluloses modified with at least one group comprising at least one fatty chain, such as alkyl, arylalkyl and alkylaryl groups, and mixtures thereof, and wherein the alkyl groups are chosen, for example, from $C_8$-$C_{22}$ alkyl groups, such as the product Natrosol Plus Grade 330 CS ($C_{16}$ alkyls) sold by the company Aqualon, and the product Bermocoll EHM 100 sold by the company Berol Nobel, and celluloses modified with at least one polyalkylene glycol alkylphenyl ether group, such as the product Amercell Polymer HM-1500 (polyethylene glycol (15) nonylphenyl ether) sold by the company Amerchol;

(2) hydroxypropyl guars modified with at least one group comprising at least one fatty chain chosen from $C_8$-$C_{22}$ fatty chains, such as the product Jaguar XC-95/3 ($C_{14}$ alkyl chain) sold by the company Rhodia, the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc;

(3) copolymers of vinylpyrrolidone and of hydrophobic monomers comprising at least one fatty chain; mention may be made, for example, of:

the products Antaron V216 and Ganex V216 (vinylpyrrolidone/hexadecene copolymer) sold by the company I.S.P., and the products Antaron V220 and Ganex V220 (vinylpyrrolidone/eicosene copolymer) sold by the company I.S.P.;

(4) copolymers of monomers chosen from $C_1$-$C_6$ alkyl acrylates and methacrylates and of amphiphilic monomers comprising at least one fatty chain;

(5) copolymers of monomers chosen from hydrophilic acrylates and methacrylates and of hydrophobic monomers comprising at least one fatty chain, such as the polyethylene glycol methacrylate/lauryl methacrylate copolymer;

(6) polymers with an aminoplast ether skeleton comprising at least one fatty chain, such as the Pure Thix compounds sold by the company Sud-Chemie; and (7) polyurethane polyethers comprising in their chain both hydrophilic blocks usually of polyoxyethylenated nature, and hydrophobic blocks that may be chains chosen from aliphatic chains, cycloaliphatic chains, and aromatic chains.

For example, the polyurethane polyethers comprise at least two hydrocarbon-based lipophilic chains, comprising from 6 to 30 carbon atoms, separated by a hydrophilic block, wherein the hydrocarbon-based chains are possibly pendent chains or chains at the end of a hydrophilic block. It is possible for at least one pendent chain to be provided. In addition, the polymer may comprise at least one hydrocarbon-based chain at one or both ends of a hydrophilic block.

The polyurethane polyethers may be multiblock, for example, in triblock form. The hydrophobic blocks may be at each end of the chain (for example: triblock copolymer comprising a hydrophilic central block) or distributed both at the ends and in the chain (for example multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups. The nonionic polyurethane polyethers comprise at least one urethane bond between the hydrophilic blocks, whence arises the name.

Among the fatty-chain nonionic polyurethane polyethers, mention may be made, for example of those whose hydrophilic blocks are linked to the lipophilic blocks via at least one other chemical bond.

Among the fatty-chain nonionic polyurethane polyethers, mention may be made, for example, of Ser-Ad FX 1100 from the company Servo Delden, which is a copolymer known under the European and US INCI name "Steareth-100/PEG-136/HMDI Copolymer".

Rheolate 205 containing a urea function, sold by the company Rheox, Rheolates 208, 204 and 212, and Acrysol RM 184, may also be used.

Mention may also be made, for example, of the product Elfacos T210 comprising at least one alkyl chain chosen from $C_{12-14}$ alkyl chains and the product Elfacos T212 containing a $C_{18}$ alkyl chain, from Akzo.

The polyurethane polyethers that may be used are, for example, those described in the article by G. Fonnum, J. Bakke and Fk. Hansen, *Colloid Polym. Sci.* 271, 380-389 (1993).

Polyurethane polyethers comprising at least one fatty chain chosen from $C_{10}$-$C_{20}$ fatty chains, and hydroxypropyl guars modified with at least one group comprising at least one fatty chain chosen from $C_8$-$C_{22}$ fatty chains, can, for example, be used.

Anionic Amphiphilic Polymers Comprising at Least One Fatty Chain

The anionic amphiphilic polymers comprising at least one fatty chain are chosen from crosslinked and non-crosslinked polymers comprising:

at least one hydrophilic unit derived from at least one monomer comprising ethylenic unsaturation bearing at least one functional group chosen from free carboxylic acid functional groups, and free, partially and totally neutralized sulphonic functional groups, and at least one hydrophobic unit derived from at least one monomer comprising ethylenic unsaturation bearing at least one hydrophobic side chain, and optionally at least one crosslinking unit derived from at least one polyunsaturated monomer.

The at least one monomer comprising ethylenic unsaturation bearing at least one carboxylic acid functional group is chosen from ethacrylic acid, methacrylic acid, and acrylic acid.

The at least one monomer comprising ethylenic unsaturation bearing at least one hydrophobic side chain can be chosen from (i) fatty alkyl esters of unsaturated carboxylic acids, and (ii) allyl fatty alkyl ethers.

(i) The fatty alkyl esters of unsaturated carboxylic acids are chosen, for example, from $C_{10-30}$, such as $C_{12-22}$, alkyl ethacrylates, methacrylates and acrylates. For example, lauryl acrylate, stearyl acrylate, decyl acrylate, isodecyl acrylate and dodecyl acrylate, as well as the corresponding methacrylates, i.e., lauryl methacrylate, stearyl methacrylate, decyl methacrylate, isodecyl methacrylate and dodecyl methacrylate can be used.

(ii) The allyl fatty alkyl ethers forming the hydrophobic units of the anionic amphiphilic polymers correspond to the following formula (I):

$$CH_2=CR'CH_2OB_nR \qquad (I)$$

in which R' is chosen from a hydrogen atom and $CH_3$; B is an ethylenoxy group; n is 0 or an integer ranging from 1 to 100; R is a hydrocarbon-based group chosen from alkyl, arylalkyl, aryl, alkylaryl and cycloalkyl radicals comprising from 8 to 30 carbon atoms, such as from 10 to 24 carbon atoms, and further such as from 12 to 18 carbon atoms. One unit of formula (I), for example, is a unit in which R' is a hydrogen atom; n is equal to 10; and R is a stearyl ($C_{18}$) radical.

The at least one crosslinking unit is chosen, for example, from compounds comprising at least two non-conjugated polymerizable double bonds. Examples that may be mentioned are diallyl phthalate, allyl (meth)acrylate, divinylbenzene, (poly)ethylene glycol dimethacrylate, methylenebisacrylamide, polyallylsucrose, and polyallylpentaerythritol.

Anionic amphiphilic polymers of the type described above are described and prepared, for example, in U.S. Pat. Nos. 3,915,921 and 4,509,949 (copolymers of (meth)acrylic acid and of $C_{10-30}$ alkyl (meth)acrylates), or in patent EP-0 216 479 B2 (copolymers of (meth)acrylic acid and of allyl fatty alkyl ethers).

Examples of the anionic amphiphilic polymers that may be used are:

- crosslinked polymers of acrylic acid and of $C_{10-30}$ alkyl methacrylate, such as Carbopol ETD 2020 sold by the company Goodrich;
- crosslinked polymers of acrylic acid and of $C_{10-30}$ alkyl acrylate, such as the polymers sold under the names Carbopol 1382, Pemulen TR1 and Pemulen TR2 by the company Goodrich;
- methacrylic acid/ethyl acrylate/oxyethylenated stearyl methacrylate (55/35/10) terpolymer;
- (meth)acrylic acid/ethyl acrylate/25 EO oxyethylenated behenyl methacrylate terpolymer, and
- methacrylic acid/ethyl acrylate/steareth-10 allyl ether crosslinked terpolymer.

The amphiphilic polymers comprising as hydrophilic units at least one ethylenically unsaturated monomer comprising at least one sulphonic functional group, in a form chosen from free, partially and totally neutralized forms, and at least one hydrophobic unit, are described, for example, in French patent applications Nos. 0 016 954 and 0 100 328.

Among these amphiphilic polymers, mention may, for example, be made of: 2-acrylamido-2-methylpropanesulphonic acid (AMPS)/n-dodecylacrylamide copolymer neutralized with sodium hydroxide, the copolymer crosslinked with methylenebisacrylamide consisting of 75% by weight of AMPS units neutralized with $NH_3$ and of 25% by weight of acrylate units of Genapol T-250, the copolymer crosslinked with allyl methacrylate consisting of 90% by weight of AMPS units neutralized with $NH_3$ and of 10% by weight of methacrylate units of Genapol T-250, and the copolymer crosslinked with allyl methacrylate consisting of 80% by weight of AMPS units neutralized with $NH_3$ and of 20% by weight of methacrylate units of Genapol T-250.

In the bleaching pastes disclosed herein, the at least one amphiphilic polymer chosen from nonionic and anionic amphiphilic polymers comprising at least one fatty chain may be present in a concentration ranging, for example, from 0.01% to 30% and such as from 0.01% to 15% by weight relative to the total weight of the bleaching paste.

Other Adjuvants

The bleaching paste disclosed herein may further comprise at least one additional adjuvant chosen from water-soluble thickening polymers, fillers such as clays and amorphous silica, binders such as vinylpyrrolidone, lubricants, for example, polyol stearates, alkali metal and alkaline-earth metal stearates, and agents for controlling the release of oxygen, such as magnesium carbonate and magnesium oxide, colorants and matting agents, for example titanium oxides, and anionic, nonionic, cationic and amphoteric surfactants.

Water-soluble Thickening Polymers

As disclosed herein, the water-soluble thickening polymers are chosen from any water-soluble polymers, which are synthetic or of natural origin, conventionally used in the cosmetic field, other than the at least one amphiphilic polymer chosen from nonionic and anionic amphiphilic polymers comprising at least one fatty chain described above.

Among synthetic water-soluble polymers, mention may be made, for example, of polyvinylpyrrolidone, polyacrylic acid, polyacrylamide, non-crosslinked poly-2-acrylamidopropanesulphonic acid such as the product sold under the name Simugel EG by the company SEPPIC, crosslinked poly-2-acrylamido-2-methylpropanesulphonic acid, poly2-acrylamido-2-methylpropanesulphonic acid crosslinked and partially neutralized with aqueous ammonia, sold under the brand name Hostacerin AMPS by the company Clariant, mixtures with a synergistic thickening effect of the non-crosslinked poly-2-acrylamido-2methylpropanesulphonic acid with hydroxyalkylcellulose ethers or with poly(ethylene oxide), as described in U.S. Pat. No. 4,540,510, and mixtures with a synergistic thickening effect of a poly(meth)acrylamido($C_1$-$C_4$)alkylsulphonic acid, such as crosslinked with a crosslinked copolymer of maleic anhydride, and of a ($C_1$-$C_5$) alkyl vinyl ether such as the mixture Hostacerin AMPS/Stabileze QM (from the company ISF) and as described in French patent application No. 0 014 416.

The thickening polymers of natural origin that may be used are, for example, chosen from polymers comprising at least one sugar unit, chosen, for example, from: nonionic guar gums; biopolysaccharide gums of microbial origin such as scleroglucan gum and xanthan gum; gums derived from plant exudates, such as gum arabic, ghatti gum, karaya gum, gum tragacanth, carrageenan, agar and carob gum; pectins; alginates; starches; hydroxy($C_1$-$C_6$)alkylcelluloses and carboxy ($C_1$-$C_6$)alkylcelluloses.

As disclosed herein, the term "sugar unit" means a monosaccharide portion, ie., monosaccharide, oside or simple sugar), an oligosaccharide portion, i.e., short chains formed from the linking of monosaccharide units, which may be different, or a polysaccharide portion, i.e., long chains consisting of monosaccharide units, which may be different, for example, polyholosides and polyosides (homopolyosides and heteropolyosides). The saccharide units can also be substituted with at least one radical chosen, for example, from alkyl, hydroxyalkyl, alkoxy, acyloxy and carboxyl radicals. For example, the saccharide units can be substituted with at least one radical chosen from alkyl radicals comprising from 1 to 4 carbon atoms.

The nonionic guar gums can be modified or unmodified.

The unmodified nonionic guar gums are, for example, the products sold under the name Guargel D/15 by the company Goodrich, Vidogum GH 175 by the company Unipectine and under the names Meypro-Guar 50 and Jaguar C by the company Meyhall.

The modified nonionic guar gums are, for example, modified with at least one group chosen from $C_1$-$C_6$ hydroxyalkyl groups.

The hydroxyalkyl groups that may be used, for example, are hydroxymethyl, hydroxyethyl, hydroxypropyl and hydroxybutyl groups.

These guar gums are well known in the state of the art and can be prepared, for example, by reacting the corresponding alkene oxides, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functional groups present on the guar gum, ranges, for example, from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

The biopolysaccharide gums of microbial origin, such as the scleroglucan and xanthan gums, the gums derived from plant exudates such as gum arabic, ghatti gum, karaya gum, gum tragacanth, carrageenan gum, agar gum and carob gum, the hydroxyalkylcelluloses and carboxymethylcelluloses, pectins, alginates and starches are well known to those skilled in the art and are described, for example, in the book by Robert L. Davidson entitled "Handbook of Water-Soluble Gums and Resins" published by McGraw Hill Book Company (1980).

Among these gums, the scleroglucans are chosen, for example, from the products sold under the name Actigum CS by the company Sanofi Bio Industries, such as Actigum CS 11, and under the name Amigel by the company Alban Muller International. Other scleroglucans, such as those treated with glyoxal in French patent application No. 2 633 940, can also be used.

The xanthans are chosen, for example, from the products sold under the names Keltrol, Keltrol T, Keltrof T F, Keltrol B T, Keltrol R D and Keltrol C G by the company Nutrasweet Kelco, and under the names Rhodicare S and Rhodicare H by the company Rhodia Chimie.

The starch derivatives that may be used, for example, are the product sold under the name Primogel by the company Avebe.

The hydroxy($C_1$-$C_6$)alkylcelluloses, for example, hydroxyethylcelluloses, such as those sold under the names Cellosize QP3L, Cellosize QP4400H, Cellosize QP30000H, Cellosize HEC30000A and Cellosize Polymer PCG10 by the company Amerchol, and Natrosol 250HHR, Natrosol 250MR, Natrosol 250M, Natrosol 250HHXR, Natrosol 250HHX, Natrosol 250HR and Natrosol HX by the company Hercules, and Tylose H1 000 by the company Hoechst can be used.

The hydroxy($C_1$-$C_6$)alkylcelluloses, for example, hydroxypropylcelluloses such as the products sold under the names Klucel E F, Klucel H, Klucel L H F, Klucel M F and Klucel G by the company Aqualon can also be used.

The carboxy($C_1$-$C_6$)alkylcelluloses, for example, carboxymethylcellulose, such as the products sold under the names Blanose 7M8/SF, Blanose Raffinée 7M, Blanose 7LF, Blanose 7MF, Blanose 9M31F, Blanose 12M31XP, Blanose 12M31P, Blanose 9M31XF, Blanose 7H, Blanose 7M31 and Blanose 7H3SXF by the company Aqualon, Aquasorb A500 and Ambergum 1221 by the company Hercules, Cellogen HP810A and Cellogen HP6HS9 by the company Montello, and Primellose by the company Avebe can be used.

When they are present in the bleaching pastes disclosed herein, the water-soluble thickening polymers are present in a weight proportion ranging from 0.01% to 30%, such as from 0.01% to 15% by weight, relative to the total weight of the paste.

Surfactants

The surfactants that can be used are chosen, for example, from the following surfactants:

Anionic Surfactants

Among the anionic surfactants which can be used, alone or as mixtures, mention may be made, for example, of salts, such as alkali metal salts, for example, sodium salts, ammonium salts, amine salts, amino alcohol salts and magnesium salts, of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$-$C_{24}$)alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulphosuccinates, alkylsulphosuccinamates; acyl isethionates and N-acyl taurates, wherein the alkyl or acyl radical of all of these different compounds comprises, for example, from 12 to 20 carbon atoms and the aryl radical is chosen, for example, from phenyl and benzyl groups. Among the anionic surfactants, which can be used, mention may also be made of fatty acid salts such as oleic, ricinoleic and palmitic acid salts, coconut oil acid and hydrogenated coconut oil acid such as the sodium, calcium and magnesium salts of stearic acid; acyl lactylates in which the acyl radical comprises from 8 to 20 carbon atoms. It is also possible to use alkyl D-galactoside uronic acids and the salts thereof, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and the salts thereof, such as those comprising from 2 to 50 alkylene oxide groups, for example, ethylene oxide groups, and mixtures thereof.

Nonionic Surfactants:

The nonionic surfactants are those that are well known per se (see, for example, "Handbook of Surfactants" by M. R. Porter, published by Blackie & Son (Glasgow and London), 1991, pp. 116-178). They can be chosen, for example, from polyethoxylated, polypropoxylated, alkylphenols, alpha-diols and alcohols comprising at least one fatty chain comprising, for example, from 8 to 18 carbon atoms, wherein it is possible for the number of the ethylene oxide group or the propylene oxide group to range, for example, from 2 to 50. Mention may also be made of copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising, for example, from 1 to 5, such as from 1.5 to 4, glycerol groups; polyethoxylated fatty amines comprising, for example, from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides and N-acylaminopropylmorpholine oxides.

Amphoteric and Zwitterionic Surfactants:

The amphoteric and zwitterionic surfactants can be chosen, for example, from aliphatic secondary and tertiary amine derivatives in which the aliphatic radical is chosen from linear and branched chains comprising from 8 to 18 carbon atoms and at least one water-solubilizing anionic group chosen, for example, from carboxylate, sulphonate, sulphate, phosphate and phosphonate; mention may also be made of ($C_8$-$C_{20}$)alkylbetaines, sulphobetaines, ($C_8$-$C_{20}$)alkylamido($C_1$-$C_6$)alkylbetaines and ($C_8$-$C_{20}$)alkylamido($C_1$-$C_6$)alkylsulphobetaines.

Among the amine derivatives, mention may be made, for example, of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the following respective formulae:

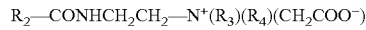

in which: $R_2$ is chosen from alkyl radicals of acids $R_2$—COOH present in hydrolysed coconut oil, heptyl, nonyl and undecyl radicals; $R_3$ is a beta-hydroxyethyl group; and $R_4$ is a carboxymethyl group; and

in which:
B is chosen from groups —$CH_2CH_2OX'$; C is chosen from groups —$(CH_2)_z$—Y', with z=1 or 2,
X' is chosen from —$CH_2CH_2$—COOH group and a hydrogen atom,
Y' is chosen from —COOH and —$CH_2$—CHOH—$SO_3H$ groups, R$_2$' is chosen from alkyl radicals of acids R$_2$'—COOH present in coconut oil and acids R$_2$'—COOH present in hydrolysed linseed oil, alkyl radicals, such as C$_7$, C$_9$, C$_{11}$, and C$_{13}$ alkyl radicals, a C$_{17}$ alkyl radical and its iso form, and an unsaturated C$_{17}$ radical.

These compounds are classified in the CTFA dictionary, 5th edition, 1993, under the names Disodium Cocoamphodiacetate, Disodium Lauroampho-diacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranole® C2M concentrate by the company Rhodia Chimie.

Cationic Surfactants:

Among the cationic surfactants, mention may be made, for example, of: salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxyalkyl-ammonium and alkylpyridinium chlorides and bromides; imidazoline derivatives; and amine oxides of cationic nature.

When they are present, the surfactants are in an amount ranging from 0.01% to 40% such as from 0.1% to 30% by weight relative to the total weight of the paste.

The bleaching paste disclosed herein may further comprise at least one conditioning polymer chosen from anhydrous cationic and amphoteric conditioning polymers that are well known to those skilled in the art and that are described in French patents Nos. 2 788 974 and 2 788 976 and as described below.

Cationic Polymers

As disclosed herein, the term "cationic polymer" means any polymer containing cationic groups and/or groups which may be ionized into cationic groups.

The cationic polymers which may be used may be chosen from any of those already known per se as improving the cosmetic properties of the hair, such as those described in patent application EP-A-337 354 and in French Patent Nos. 2 270 846, 2 383 660, 2 598 611, 2 470 596 and 2 519 863.

For example, the cationic polymers can be chosen from those comprising units comprising at least one amine group chosen from primary, secondary, tertiary, and quaternary amine groups, which may either form part of the main polymer chain or may be borne by a side substituent directly attached thereto.

The cationic polymers used have a number-average molecular mass ranging, for example, from 500 and 5×10$^6$, such as from 10$^3$ to 3×10$^6$.

Among the cationic polymers which may be used mention may be made, for example, of polymers of the polyamine, polyamino amide and polyquaternary ammonium type.

These polymers are known products. They are described, for example, in French Patent Nos. 2 505 348 and 2 542 997. These polymers may be chosen, for example, from:

(1) Homopolymers and copolymers derived from acrylic and methacrylic esters and amides and comprising at least one unit chosen from the units of formulae (I), (II), (III) and (IV) below:

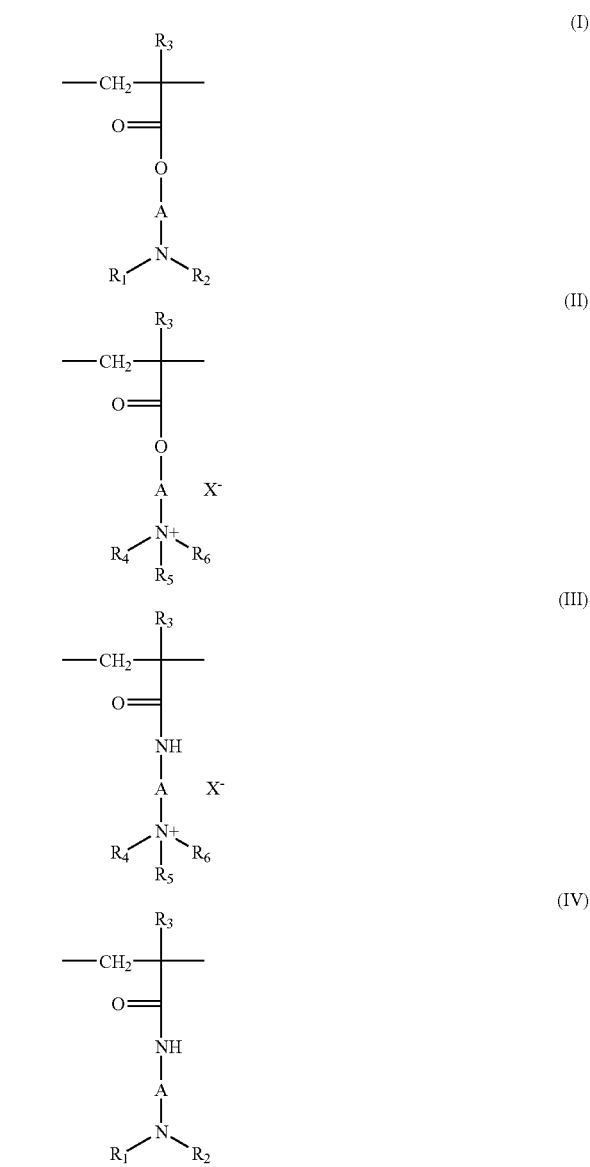

in which:
R$_3$, which may be identical or different, is chosen from a hydrogen atom and a CH$_3$ radical; A, which may be identical or different, is chosen from linear and branched alkyl groups comprising from 1 to 6 carbon atoms, such as 2 and 3 carbon atoms, and hydroxyalkyl groups comprising from 1 to 4 carbon atoms;

R$_4$, R$_5$ and R$_6$, which may be identical or different, are each chosen from alkyl groups comprising from 1 to 18 carbon atoms, such as from 1 to 6 carbon atoms, and a benzyl radical;

R$_1$ and R$_2$, which may be identical or different, are each chosen from hydrogen and alkyl groups comprising from 1 to 6 carbon atoms, such as methyl and ethyl; and X$^-$ is an anion chosen from anions derived from acids chosen from inorganic and organic acids, such as a methosulphate anion and halides such as chloride and bromide.

The polymers of family (1) can also comprise at least one unit derived from comonomers, which may be chosen from acrylamides, methacrylamides, diacetone acrylamides, acrylamides, and methacrylamides substituted on the nitrogen with at least one radical chosen from lower ($C_1$-$C_4$) alkyl radicals, acrylic and methacrylic acids and esters thereof, vinyllactams such as vinylpyrrolidone and vinylcaprolactam, and vinyl esters.

Among these polymers of family (1), mention may be made, for example, of:

- copolymers of acrylamide and of dimethylaminoethyl methacrylate quaternized with at least one entity chosen from dimethyl sulphates and dimethyl halides;
- the copolymers of acrylamide and of methacryloyloxyethyltrimethylammonium chloride described, for example, in patent application EP-A-080 976;
- copolymers of acrylamide and of methacryloyloxyethyltrimethylammonium methosulphate;
- quaternized and non-quaternized vinylpyrrolidone/dialkylaminoalkyl acrylate and methacrylate copolymers. These polymers are described in French Patent Nos. 2 077 143 and 2 393 573;
- dimethylaminoethyl methacrylate/vinylcaprolactam/vinylpyrrolidone terpolymers;
- vinylpyrrolidone/methacrylamidopropyldimethylamine copolymers; and
- quaternized vinylpyrrolidone/dimethylaminopropylmethacrylamide copolymers.

(2) The cellulose ether derivatives comprising at least one quaternary ammonium group, described in French Patent No. 1 492 597. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers and cellulose derivatives grafted with at least one water-soluble monomer of quaternary ammonium, and described, for example, in U.S. Pat. No. 4,131,576, such as hydroxyalkylcelluloses, for example, hydroxymethyl-, hydroxyethyl- and hydroxypropylcelluloses grafted, for example, with at least one salt chosen from methacryloylethyltrimethylammonium, methacrylamidopropyltrimethylammonium and dimethyldiallylammonium salts.

(4) The cationic polysaccharides described, for example, in U.S. Pat. Nos. 3,589,578 and 4,031,307, such as guar gums comprising at least one cationic trialkylammonium group. Guar gums modified with at least one salt (e.g. chloride) of 2,3-epoxypropyltrimethylammonium can, for example, be used.

(5) Polymers comprising piperazinyl units and radicals chosen from divalent alkylene and hydroxyalkylene radicals comprising at least one chain chosen from straight and branched chains, optionally interrupted by at least one entity chosen from oxygen, sulphur and nitrogen atoms and aromatic and heterocyclic rings, as well as the oxidation and/or quaternization products of these polymers. Such polymers are described, for example, in French Patent Nos. 2 162 025 and 2 280 361;

(6) Water-soluble polyamino amides prepared, for example, by polycondensation of an acidic compound with a polyamine; these polyamino amides can be crosslinked with at least one agent chosen from epihalohydrins, diepoxides, dianhydrides, unsaturated dianhydrides, bis-unsaturated derivatives, bis-halohydrins, bis-azetidiniums, bis-haloacyldiamines, bis-alkyl halides and oligomers resulting from the reaction of a difunctional compound, which is reactive with at least one entity chosen from bis-halohydrins, bis-azetidiniums, bis-haloacyldiamines, bis-alkyl halides, epihalohydrins, diepoxides and bis-unsaturated derivatives; the crosslinking agent being used in a proportion ranging from 0.025 to 0.35 mol per amine group of the polyamino amide; these polyamino amides can be alkylated or, if they comprise at least one tertiary amine functional group, they can be quaternized. Such polymers are described, for example, in French Patent Nos. 2 252 840 and 2 368 508;

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms chosen, for example, from methyl, ethyl and propyl. Such polymers are described, for example, in French Patent No. 1 583 363. Among these derivatives, mention may be made, for example, of the adipic acid/dimethylaminohydroxypropyl/diethylenetriamine polymers.

(8) The polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

(9) Cyclopolymers of alkyldiallylamine and of dialkyldiallylammonium, such as the homopolymers and copolymers containing, as main constituent of the chain, units corresponding to formulae (V) and (VI):

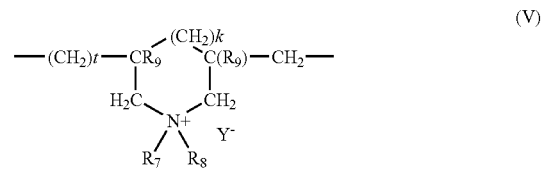

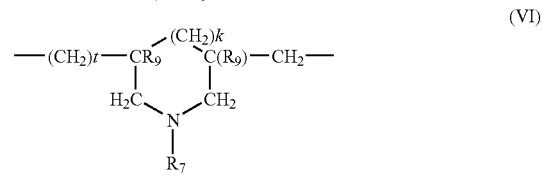

in which k and t, which may be identical or different, are each equal to 0 or 1, the sum k+t being equal to 1; $R_9$ is chosen from a hydrogen atom and a methyl radical; $R_7$ and $R_8$, which may be identical or different, are each chosen from alkyl groups comprising from 1 to 22 carbon atoms, hydroxyalkyl groups in which the alkyl group comprises from 1 to 5 carbon atoms, and lower $C_1$-$C_4$ amidoalkyl groups, or $R_7$ and $R_8$ can form, together with the nitrogen atom to which they are attached, a heterocyclic group such as piperidyl and morpholinyl; in one embodiment, $R_7$ and $R_8$, which may be identical or different, are each chosen from alkyl groups comprising from 1 to 4 carbon atoms; $Y^-$ is an anion such as bromide, chloride, acetate, borate, citrate, tartrate, bisulphate, bisulphite, sulphate and phosphate. These polymers are described, for example, in French Patent No. 2 080 759 and in its Certificate of Addition 2 190 406.

(10) The quaternary diammonium polymers comprising repeating units corresponding to the formula (VII):

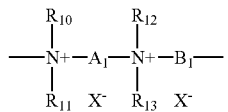
(VII)

in which:

$R_{10}$, $R_{11}$, $R_{12}$ and $R_{13}$, which may be identical or different, are each chosen from aliphatic, alicyclic and arylaliphatic radicals comprising from 1 to 20 carbon atoms and lower hydroxyalkylaliphatic radicals, or alternatively $R_{10}$, $R_{11}$, $R_{12}$ and $R_{13}$, together or separately, form, with the nitrogen atoms to which they are attached, heterocycles optionally comprising at least one second hetero atom other than nitrogen, or alternatively $R_{10}$, $R_{11}$, $R_{12}$ and $R_{13}$ are chosen from linear and branched $C_1$-$C_6$ alkyl radicals substituted with at least one group chosen from nitrile, ester, acyl and amide groups and groups —CO—O—$R_{14}$—D and —CO—NH—$R_{14}$—D, wherein $R_{14}$ is chosen from alkylenes and D is a quaternary ammonium group;

$A_1$ and $B_1$, which may be identical or different, are each chosen from polymethylene groups comprising from 2 to 20 carbon atoms which may be linear or branched, saturated or unsaturated, and which may comprise, linked to or intercalated in the main chain, at least one entity chosen from aromatic rings, oxygen and sulphur atoms, and sulphoxide, sulphone, disulphide, amino, alkylamino, hydroxyl, quaternary ammonium, ureido, amide and ester groups, and $X^-$ is an anion chosen from anions derived from acids chosen from inorganic and organic acids;

$A_1$, $R_{10}$ and $R_{12}$ can form, with the two nitrogen atoms to which they are attached, a piperazine ring; in addition, if $A_1$ is chosen from linear and branched, saturated and unsaturated alkylene and hydroxyalkylene radicals, $B_1$ can also be chosen from groups —$(CH_2)_n$—CO—D—OC—$(CH_2)_n$— in which n ranges from 1 to 100 such as from 1 to 50, and D is chosen from:

a) glycol residues of formula: —O—Z—O—, wherein Z is chosen from linear and branched hydrocarbon-based radicals and groups corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— wherein x and y, which may be identical or different, are each an integer from 1 to 4, representing a defined and unique degree of polymerization or any number from 1 to 4, representing an average degree of polymerization;

b) bis-secondary diamine residues such as piperazine derivatives;

c) bis-primary diamine residues of formula: —NH—Y—NH—, wherein Y is chosen from linear and branched hydrocarbon-based radicals and a divalent radical —CH$_2$—CH$_2$—S—S—CH$_2$—CH$_2$—; and d) a ureylene group of formula: —NH—CO—NH—.

In one embodiment, $X^-$ is an anion chosen, for example, from chloride and bromide.

These polymers generally have a number-average molecular mass ranging from 1000 to 100,000.

Polymers of this type are described, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is, for example, possible to use polymers that comprise repeating units corresponding to the following formula (VIII):

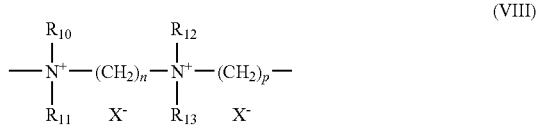
(VIII)

in which $R_{10}$, $R_{11}$, $R_{12}$ and $R_{13}$, which may be identical or different, are chosen from alkyl and hydroxyalkyl radicals comprising from 1 to 4 carbon atoms, n and p, which may be identical or different, are each an integer chosen from integers ranging from 2 to 20, and $X^-$ is an anion chosen from anions derived from acids chosen from inorganic and organic acids.

(11) Polyquaternary ammonium polymers comprising repeating units of formula (IX):

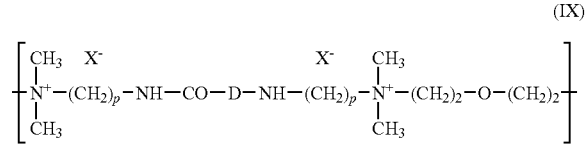
(IX)

in which p is an integer chosen from integers ranging from 1 to 6, D may be nothing or may be chosen from groups —$(CH_2)_r$—CO— in which r is a number equal to 4 or 7, and $X^-$ is an anion;

Such polymers may be prepared according to the processes described in U.S. Pat. Nos. 4,157,388, 4,702,906 and 4,719,282. They are described, for example, in patent application EP-A-122 324.

(12) Quaternary polymers of vinylpyrrolidone and of vinylimidazole.

(13) Polyamines such as the product that is given under the reference name "Polyethylene glycol (15) Tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. A crosslinked acrylamide/methacryloyloxyethyltrimethylammonium chloride copolymer (20/80 by weight) in the form of a dispersion containing 50% by weight of the copolymer in mineral oil can, for example, be used. This dispersion is sold under the name "Salcare® SC 92" by the company Allied Colloids. A crosslinked methacryloyloxyethyltrimethylammonium chloride homopolymer containing 50% by weight of the homopolymer in mineral oil or in a liquid ester can also be used.

These dispersions are sold under the names "Salcare® SC 95" and "Salcare® SC 96" by the company Allied Colloids.

Other cationic polymers which can be used are, for example, polyalkyleneimines, such as polyethyleneimines, polymers comprising at least one unit chosen from vinylpyridine and vinylpyridinium units, condensates of polyamines and of epichlorohydrin, quaternary polyureylenes and chitin derivatives.

Amphoteric Polymers

The amphoteric polymers, which may be used, may be chosen from polymers comprising units K and M randomly distributed in the polymer chain, in which K is a unit derived from a monomer comprising at least one basic nitrogen atom and M is a unit derived from an acidic monomer comprising at least one group chosen from carboxylic and sulphonic groups, or alternatively K and M may be chosen from groups derived from zwitterionic carboxybetaine and sulphobetaine monomers;

K and M may also be chosen from cationic polymer chains comprising at least one amine group chosen from primary, secondary, tertiary and quaternary amine groups, in which at least one of the amine groups bears at least one group chosen from carboxylic and sulphonic groups linked via a hydrocarbon-based radical, or alternatively K and M form part of a chain of a polymer comprising at least one α,β-dicarboxylic ethylene unit in which one of the carboxylic groups has been made to react with a polyamine comprising at least one amine group chosen from primary and secondary amine groups.

The amphoteric polymers corresponding to the above definition can be, for example, chosen from the following polymers:

(1) Polymers resulting from the copolymerization of a monomer derived from a vinyl compound bearing at least one carboxylic group such as acrylic acid, methacrylic acid, maleic acid, and α-chloroacrylic acid, and of a basic monomer derived from a substituted vinyl compound comprising at least one basic atom, such as dialkylaminoalkyl methacrylate and acrylate, dialkylaminoalkylmethacrylamide and -acrylamide. Such polymers are described, for example, in U.S. Pat. No. 3,836,537. Mention may also be made of the sodium acrylate/acrylamidopropyltrimethylammonium chloride copolymer.

The vinyl compound may also be a dialkyldiallylammonium salt such as dimethyldiallylammonium chloride.

(2) Polymers comprising at least one unit derived from:
a) at least one monomer chosen from acrylamides and methacrylamides substituted on the nitrogen with at least one alkyl radical,
b) at least one acidic comonomer comprising at least one reactive carboxylic group, and
c) at least one basic comonomer such as esters comprising at least of primary, secondary, tertiary and quaternary amine substituents of acrylic and methacrylic acids and the product of quaternization of dimethylaminoethyl methacrylate with dimethyl or diethyl sulphate.

The N-substituted acrylamides and methacrylamides are, for example, groups in which the alkyl radicals comprise from 2 to 12 carbon atoms such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acid, methacrylic acid, crotonic acid, itaconic acid, maleic acid and fumaric acid and alkyl monoesters, comprising from 1 to 4 carbon atoms, of maleic and fumaric acids and anhydrides.

The basic comonomers are chosen, for example, from aminoethyl, butylaminoethyl, N,N'-dimethylaminoethyl and N-tert-butylaminoethyl methacrylates.

(3) Crosslinked and alkylated polyamino amides partially or totally derived from polyamino amides of general formula:

$$-[CO-R_{19}-CO-Z]- \quad (X)$$

in which $R_{19}$ is a divalent radical derived from an entity chosen from saturated dicarboxylic acids, mono- and dicarboxylic aliphatic acids comprising an ethylenic double bond, esters of a lower alkanol chosen from those comprising from 1 to 6 carbon atoms, and of these acids, and radicals derived from the addition of any one of these acids to a bis(primary) or bis(secondary) amine, and Z is a radical chosen from bis(primary), mono- and bis(secondary) polyalkylene-polyamine radicals such as:

a) in a proportion ranging from 60 to 100 mol %, the radical (XI)

$$-\underset{H}{N}-[(CH_2)_x-\underset{H}{N}]_p- \quad (XI)$$

wherein x=2 and p=2 or 3, or x=3 and p=2;

this radical being derived from diethylenetriamine, from triethylenetetraamine or from dipropylenetriamine;

b) in a proportion ranging from 0 to 40 mol %, the radical (XI) above in which x=2 and p=1 and which is derived from ethylenediamine, or the radical derived from piperazine:

c) in a proportion ranging from 0 to 20 mol %, the —NH—$(CH_2)_6$—NH— radical derived from hexamethylenediamine, these polyaminoamines being crosslinked by addition of at least one difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of an entity chosen from acrylic acids, chloroacetic acids and alkane sultones, and salts thereof.

The saturated carboxylic acids are, for example, chosen from acids comprising from 6 to 10 carbon atoms, such as adipic acid, 2,2,4-trimethyladipic acid and 2,4,4-trimethyladipic acid, terephthalic acid and acids comprising an ethylenic double bond such as acrylic acid, methacrylic acid and itaconic acid.

The alkane sultones used in the alkylation are, for example, chosen from propane sultone and butane sultone, and the salts of the alkylating agents are chosen, for example, from the sodium and potassium salts.

(4) Polymers comprising zwitterionic units of formula:

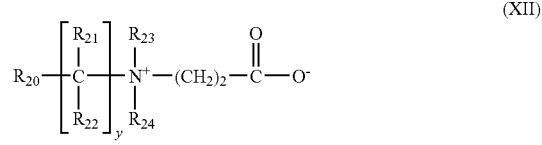

(XII)

in which $R_{20}$ is chosen from polymerizable unsaturated groups such as acrylate, methacrylate, acrylamide and methacrylamide groups, y and z, which may be identical or different, are each an integer ranging from 1 to 3, $R_{21}$, and $R_{22}$, which may be identical or different, are each chosen from a hydrogen atom, methyl, ethyl and propyl, $R_{23}$ and $R_{24}$, which may be identical or different, are each chosen from a hydrogen atom and alkyl radicals such that the sum of the carbon atoms in $R_{23}$ and $R_{24}$ does not exceed 10.

The polymers comprising such units can also comprise units derived from non-zwitterionic monomers such as dimethyl and diethylaminoethyl acrylate and methacrylate, alkyl acrylates and methacrylates, acrylamides and methacrylamides, and vinyl acetate.

By way of example, mention may be made of the copolymer of butyl methacrylate/dimethyl carboxymethylammonio ethyl methacrylate such as the product sold under the name Diaformer Z301 by the company Sandoz.

(5) Polymers derived from chitosan comprising monomer units corresponding to formulae (XIII), (XIV) and (XV) below:

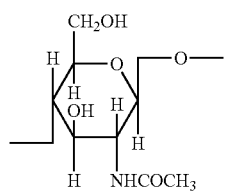

(XIII)

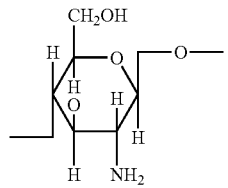

(XIV)

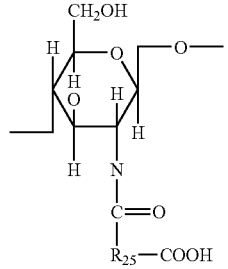

(XV)

wherein the unit (XIII) is present in a proportion ranging from 0 to 30%, the unit (XIV) in a proportion ranging from 5 to 50% and the unit (XV) in a proportion ranging from 30 to 90%, wherein in this unit (XV), $R_{25}$ is a radical of formula:

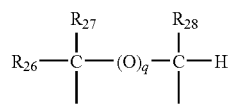

in which q is 0 or 1;

if q=0, $R_{26}$, $R_{27}$ and $R_{28}$, which may be identical or different, are each chosen from a hydrogen atom, methyl, hydroxyl, acetoxy and amino residues, monoalkylamine residues and dialkylamine residues which are optionally interrupted by at least one nitrogen atom and/or optionally substituted with at least one group chosen from amine, hydroxyl, carboxyl, alkylthio and sulphonic groups, alkylthio residues in which the alkyl group bears at least one amino residue, at least one of the radicals $R_{26}$, $R_{27}$ and $R_{28}$ being, in this case, a hydrogen atom;

or, if q=1, $R_{26}$, $R_{27}$ and $R_{28}$ are each a hydrogen atom, as well as the acid and base addition salts thereof.

(6) Polymers derived from the N-carboxyalkylation of chitosan, such as N-carboxymethylchitosan and N-carboxybutylchitosan.

(7) Polymers corresponding to the general formula (XI) as described, for example, in French Patent No. 1 400 366:

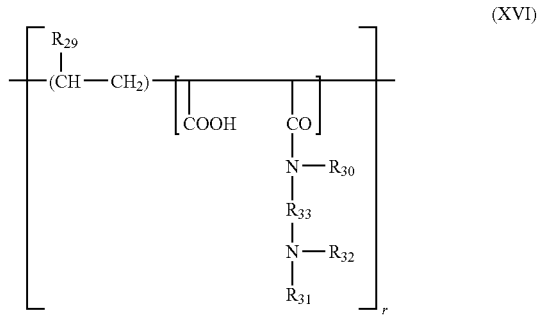

(XVI)

in which $R_{29}$ is chosen from a hydrogen atom, and $CH_3O$, $CH_3CH_2O$ and phenyl radicals, $R_{30}$ is chosen from hydrogen and lower alkyl radicals such as methyl and ethyl, $R_{31}$ is chosen from hydrogen and lower alkyl radicals such as methyl and ethyl, $R_{32}$ is chosen from lower alkyl radicals such as methyl and ethyl and radicals corresponding to the formula: $—R_{33}—N(R_{31})_2$, wherein $R_{33}$ is chosen from $—CH_2—CH_2—$, $—CH_2—CH_2—CH_2—$ and $—CH_2—CH(CH_3)—$ groups, and $R_{31}$ has the same meaning as discussed above, as well as the higher homologues of these radicals and containing up to 6 carbon atoms, r is such that the molecular weight ranges from 500 to 6 000 000 and such as from 1000 to 1 000 000.

(8) Amphoteric polymers of the type —D—X—D—X— chosen from:

a) polymers obtained by the reaction of chloroacetic acid or sodium chloroacetate with compounds comprising at least one unit of formula:

$$—D—X—D—X—D— \quad \text{(XVII)}$$

wherein D is a radical

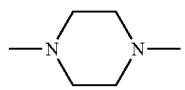

and X is chosen from symbols E and E', wherein E and E', which may be identical or different, are chosen from divalent alkylene radicals comprising at least one chain chosen from straight and branched chains comprising up to 7 carbon atoms in the main chain, wherein said divalent alkylene radicals are optionally substituted with at least one hydroxyl group. E or E' can comprise, in addition to the oxygen, at least one atom chosen from nitrogen and sulphur atoms, and from 1 to 3 rings chosen from aromatic and heterocyclic rings. The oxygen, nitrogen and sulphur atoms can be present in the form of at least one group chosen from ether, thioether, sulphoxide, sulphone, sulphonium, alkylamine, alkenylamine, hydroxyl, benzylamine, amine oxide, quaternary ammonium, amide, imide, alcohol, ester and urethane groups;

b) polymers of formula:

-D-X-D-X— (XVIII)

wherein D is a radical

and X is chosen from the symbols E and E' and wherein at least one X is E'; E having the meaning given above and E' being chosen from divalent alkylene radicals comprising at least one chain chosen from straight and branched chains comprising up to 7 carbon atoms in the main chain, wherein said divalent alkylene radicals are optionally substituted with at least one hydroxyl radical and comprising at least one nitrogen atom, wherein the nitrogen atom is substituted with an alkyl chain, wherein the alkyl chain is optionally interrupted by an oxygen atom, comprises at least one functional group chosen from carboxyl functional groups and hydroxyl functional groups, and is betainized by reaction with a reactant chosen from chloroacetic acid and sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

Among all the cationic and amphoteric polymers that may be used, mention may be made, for example, of the following polymers:

(i) among the cationic polymers:
the dimethyldiallylammonium chloride homopolymer sold under the name Merquat 100DRY by the company Merck;
the copolymers of dimethyldiallylammonium chloride and of acrylamide that are sold under the name Merquat 2200 by the company Calgon;
the polymers of poly(quaternary ammonium) type prepared and described in French Patent No. 2 270 846, comprising repeating units of formulae (W) and (U) below:

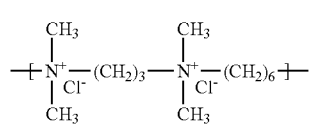

(W)

such as those whose weight-average molecular mass, determined by gel permeation chromatography, ranges from 9500 to 9900;

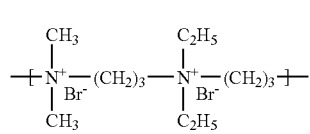

(U)

such as those whose weight-average molecular mass, determined by gel permeation chromatography, is 1200;

polymers of poly(quaternary ammonium) type of family (11) and of formula (IX) in which $X^-$ is chlorine, such as those whose weight-average molecular mass is less than 100 000 further such as less than or equal to 50 000;

(ii) among the amphoteric polymers:
the dimethyldiallylammonium chloride/acrylic acid (80/20) copolymer sold under the name Merquat 280 Dry by the company Calgon (CTFA name: Polyquaternium 22);
the dimethyldiallylammonium chloride/acrylic acid (95/5) copolymer sold under the name Merquat 295 Dry by the company Calgon (CTFA name: Polyquaternium 22);
the copolymer of methacrylamidopropyltrimonium chloride, of acrylic acid and of ethyl acrylate, sold under the name Merquat 2001 by the company Calgon (CTFA name: Polyquaternium 47); and
the acrylamide/dimethyldiallylammonium chloride/acrylic acid terpolymer sold under the name Merquat Plus 3330 Dry by the company Calgon (CTFA name: Polyquaternium 39).

When the at least one polymer chosen from cationic and amphoteric polymers is present in the bleaching pastes disclosed herein, the at least one polymer chosen from cationic and amphoteric polymers is present in a weight proportion of less than or equal to 20% relative to the total weight of the paste such as less than or equal to 8% relative to the total weight of the paste.

Preparation of the Bleaching Paste

The bleaching paste disclosed herein can be prepared by dispersing, under mechanical action, all the pulverulent compounds in the polydecene, in which the other liquid compounds of the composition have been predispersed or premixed.

The paste may also be prepared by extrusion, by introducing the liquid and solid phases of the composition into the extruder, and then mixing them at a temperature below 25° C. using a co-rotating twin-screw system comprising transportation and blending components.

The bleaching paste thus prepared is used for the preparation of a ready-to-use composition that results from the extemporaneous mixing of the paste with an aqueous hydrogen peroxide composition.

The paste is thus mixed with from 0.5 to 10 weight equivalents of an aqueous hydrogen peroxide composition, which may be a solution, an emulsion or a gel, having a weight concentration of hydrogen peroxide ranging from 2% to 12%, relative to the total weight of the aqueous hydrogen peroxide composition.

This mixing should be performed immediately before applying the product to the hair.

The aqueous hydrogen peroxide composition has, for example, a pH of less than 7.

The acidic pH can ensure the stability of the hydrogen peroxide in the composition.

The pH may be obtained by addition of at least one acidifying agent, chosen, for example, from hydrochloric acid, acetic acid, ethydronic acid, phosphoric acid, lactic acid and boric acid, and it may be conventionally adjusted by adding at least one basifying agent, chosen, for example, from aqueous ammonia, monoethanolamine, diethanolamine, triethanolamine, isopropanolamine, 1,3-diaminopropane, alkali metal and ammonium (bi)carbonates, organic carbonates such as guanidine carbonate, and alkaline hydroxides.

The aqueous hydrogen peroxide composition may also comprise at least one adjuvant chosen from preserving agents, colorants, fragrances, antifoams, hydrogen peroxide stabilizers such as sodium pyrophosphate, sodium stannate and sodium salicylate, and sequestering agents, such as ethylenediaminetetraacetic acid (EDTA) and pentasodium pentetate (CTFA name).

Needless to say, a person skilled in the art will take care to select the optional additional compound(s) mentioned above, such that the advantageous properties intrinsically associated with the anhydrous bleaching paste or with the ready-to-use bleaching composition disclosed herein are not, or are not substantially, adversely affected by the envisaged addition(s).

The pH of the ready-to-use bleaching composition ranges, for example, from 4 to 12, further, for example, from 7 to 11.5, and even further, for example, from 8 to 11.

In one embodiment, the bleaching process disclosed herein comprises mixing, immediately before use, an anhydrous paste as described herein with an aqueous hydrogen peroxide composition as described herein, applying the ready-to-use bleaching composition thus obtained to the area of wet or dry human keratin fibers to be bleached and leaving the composition to act for an action time that is sufficient to obtain the desired bleaching, such as ranging from 1 to 60 minutes and further such as from 10 to 45 minutes, and removing the bleaching mixture by rinsing with water, followed by washing with a shampoo, and then optionally drying.

The following examples illustrate the invention, without, however, being limiting in nature.

EXAMPLES OF ANHYDROUS BLEACHING PASTES 6 anhydrous pastes, 1 to 6, below for bleaching the hair were prepared (amounts expressed as grams of Active Material):

|  | Examples | | | | | |
|---|---|---|---|---|---|---|
|  | According to the invention | | | | | Prior art |
|  | 1 | 2 | 3 | 4 | 5 | 6 |
| Potassium persulphate | 36.1 | 35.9 | 36.9 | 37.1 | 36.1 | 38.3 |
| Sodium persulphate | 6 | 6 | 6 | 6 | 6 | 6 |
| Sodium disilicate | 15 | 15 | 15 | 15 | 15 | 15 |
| Ammonium chloride | 4.2 | 4.2 | 4.2 | 4.2 | 4.2 | 4.2 |
| Sodium metasilicate | 3 | 3 | 3 | 3 | 3 | 3 |
| Ammonium sulphate |  | 2 |  |  |  | 2 |
| EDTA (sequestering agent) | 0.2 | 0.2 | 0.2 | 0.2 | 0.2 | 0.2 |
| Fatty-chain nonionic amphiphilic polymer: Ser-ad FX 1100 sold by the company Servo Delden | 0.5 | 0.5 | 2 |  |  |  |
| Fatty-chain anionic amphiphilic polymer: crosslinked copolymer of acrylic acid and of $C_{10-30}$ alkyl methacrylate (Carbopol ETD 2020 sold by the company Goodrich) |  |  |  | 0.5 | 0.5 | 0.5 |
| Water-soluble thickening polymer: Primogel sold by Avebe | 1 | 1 | 2 | 1 | 1 | 1 |
| Water-soluble thickening polymer: unmodified nonionic guar gum (Guargel D/15 sold by the company Goodrich) | 0.5 | 0.5 |  |  | 0.5 | 3 |
| Xanthan gum (Keltrol BT sold by the company NutraSweet Kelco | 3 | 3 |  | 2 | 3 |  |
| Anionic surfactant: sodium cetostearyl sulphate |  |  | 1 |  |  | 2.5 |
| Anionic surfactant: sodium lauryl sulphate | 4 | 4 | 3 | 4 | 4 |  |

-continued

|  | Examples | | | | | |
|---|---|---|---|---|---|---|
|  | According to the invention | | | | | Prior art |
|  | 1 | 2 | 3 | 4 | 5 | 6 |
| Sodium stearate |  |  | 2 |  |  | 1 |
| Magnesium stearate | 2 | 2 |  | 2 | 2 |  |
| Polyvinylpyrrolidone |  |  |  |  | 0.5 | 0.5 |
| Titanium oxide | 1 | 1 | 1 | 1 | 0.5 | 1 |
| Beeswax |  |  |  |  |  | 1 |
| Colorant (ultramarine) . . . |  | 0.2 | 0.2 | 0.5 |  |  |
| Isopropyl palmitate sold under the name Isopropyl Palmitate by the company Cognis |  |  |  |  |  | 21.8 |
| Polydecene sold under the name Silkflo 366 NAS Polydecene by the company Amoco Chemical |  | 18 |  |  |  |  |
| Polydecene sold under the name Nexbase 2006 FG by the company Fortum | 18 |  | 22.5 | 22.5 | 18 |  |
| Amorphous silica |  |  | 0.5 |  |  | 1 |
| Fumed silica of hydrophobic nature (Aerosil ® R972 sold by the company the Degussa Hüls) |  | 0.5 | 0.7 |  |  |  |
| Fumed silica of hydrophilic nature (Aerosil ® 300 sold by the company Degussa Hüls) | 0.5 | 0.5 |  | 0.3 | 0.5 |  |
| Block polymer disclosed herein: sold under the name Geahlene 200 by the company Penreco | 5 | 5 |  |  | 5 |  |

The pastes of Examples 1 to 5 according to the invention were found to be less sensitive to the succession of thermal shocks and also to exposure to temperatures below 4° C. and above 45° C., than the paste of Example 6 of the prior art based on wax and on isopropyl palmitate.

In addition, the pastes of Examples 1 to 5, mixed with an aqueous 9% hydrogen peroxide composition, resulted in more powerful and more uniform bleaching, without leaving the hair greasy or coarse.

What is claimed is:

1. An anhydrous paste for bleaching human keratin fibers, comprising
    at least one peroxygenated salt,
    at least one alkaline agent,
    from 15% to 35% by weight of at least one polydecene of formula $C_{10n}H_{[(20n)+2]}$, wherein n ranges from 3 to 9, relative to the total weight of the paste, and
    from 0.01% to 10% by weight of at least one gelling agent chosen from hydrophilic fumed silicas, hydrophobic fumed silicas and diblock, triblock, multiblock and radial-block copolymers comprising at least one segment of styrene monomers and at least one segment of monomers chosen from thermoplastic monomers and comonomers, relative to the total weight of the paste;
    wherein said anhydrous paste has a water content less than 1% by weight relative to the total weight of the paste.

2. The paste according to claim 1, wherein the human keratin fibers are hair.

3. The paste according to claim 1, wherein in defining the at least one polydecene of formula $C_{10n}H_{[(20n)+2]}$, n ranges from 3 to 7.

4. The paste according to claim 1, wherein the at least one polydecene is present in a concentration ranging from 15% to 30% by weight relative to the total weight of the paste.

5. The paste according to claim 4, wherein the at least one polydecene is present in a concentration ranging from 15% to 25% by weight relative to the total weight of the paste.

6. The paste according to claim 1, wherein the at least one gelling agent is present in a concentration ranging from 0.01% to 5% by weight relative to the total weight of the paste.

7. The paste according to claim 6, wherein the at least one gelling agent is present in a concentration ranging from 0.1% to 2.5% by weight relative to the total weight of the paste.

8. The paste according to claim 1, wherein, in the block copolymers, the at least one segment of monomers chosen from thermoplastic monomers and comonomers is chosen from ethylene/$C_3$-$C_4$ alkylene segments.

9. The paste according to claim 8, wherein the block copolymers are chosen from hydrogenated block copolymers comprising at least one styrene block and at least one block chosen from ethylene/$C_3$-$C_4$ alkylene blocks.

10. The paste according to claim 1, wherein the at least one peroxygenated salt is chosen from ammonium and alkali metal persulphates, perborates and percarbonates, and magnesium peroxide.

11. The paste according to claim 10, wherein the at least one peroxygenated salt is chosen from sodium persulphate and potassium persulphate.

12. The paste according to claim 1, wherein the at least one peroxygenated salt is present in a concentration ranging from 10% to 70% by weight relative to the total weight of the paste.

13. The paste according to claim 1, wherein the at least one alkaline agent is chosen from urea, alkali metal silicates and phosphates, alkaline-earth metal silicates and phosphates, and ammonia precursors.

14. The paste according to claim 13, wherein the at least one alkaline agent is chosen from alkali metal metasilicates and ammonium salts.

15. The paste according to claim 1, wherein the at least one alkaline agent is present in a concentration ranging from 0.01% to 40% by weight relative to the total weight of the paste.

16. The paste according to claim 1, further comprising from 0.01% to 30% by weight of at least one polymer chosen from nonionic and anionic amphiphilic polymers comprising at least one fatty chain, relative to the total weight of the paste.

17. The paste according to claim 1, further comprising at least one adjuvant chosen from water-soluble thickening polymers, fillers, binders, lubricants, agents for controlling release of oxygen, colorants, matting agents, and surfactants chosen from anionic, nonionic, cationic and amphoteric surfactants.

18. An anhydrous paste for bleaching human keratin fibers, comprising:
from 10% to 70% by weight of at least one peroxygenated salt chosen from sodium persulphate and potassium persulphate, relative to the total weight of the paste,
from 0.01% to 40% by weight of at least one alkaline agent, relative to the total weight of the paste,
from 15% to 35% by weight of at least one polydecene of formula $C_{10n}H_{[(20n)+2]}$, wherein n ranges from 3 to 9, relative to the total weight of the paste, and
from 0.01% to 10% by weight of at least one gelling agent chosen from hydrophilic fumed silicas, hydrophobic fumed silicas and hydrogenated block copolymers comprising at least one styrene block and at least one block chosen from ethylene/$C_3$-$C_4$ alkylene blocks, relative to the total weight of the paste; wherein said anhydrous paste has a water content less than 1% by weight relative to the total weight of the paste.

19. The paste according to claim 18, wherein the human keratin fibers are hair.

20. The paste according to claim 18, wherein in defining the at least one polydecene of formula $C_{10n}H_{[(20n)+2]}$, n ranges from 3 to 7.

21. A method for manufacturing a ready-to-use bleaching composition comprising including in said composition at least one anhydrous paste comprising:
at least one peroxygenated salt,
at least one alkaline agent,
from 15% to 35% by weight of at least one polydecene of formula $C_{10n}H_{[(20n)+2]}$, wherein n ranges from 3 to 9, relative to the total weight of the paste, and
from 0.01% to 10% by weight of at least one gelling agent chosen from hydrophilic fumed silicas, hydrophobic fumed silicas, and diblock, triblock, multiblock and radial-block copolymers comprising at least one segment of styrene monomers and at least one segment of monomers chosen from thermoplastic monomers and comonomers, relative to the total weight of the paste; wherein said anhydrous paste has a water content less than 1% by weight relative to the total weight of the paste; and extemporaneously including in said composition at least one aqueous hydrogen peroxide composition.

22. A method for manufacturing a ready-to-use bleaching composition comprising including in said composition at least one anhydrous paste comprising
from 10% to 70% by weight of at least one peroxygenated salt chosen from sodium persulphate and potassium persulphate, relative to the total weight of the paste,
from 0.01% to 40% by weight of at least one alkaline agent, relative to the total weight of the paste,
from 15% to 35% by weight of at least one polydecene of formula $C_{10n}H_{[(20n)+2]}$, wherein n ranges from 3 to 9, relative to the total weight of the paste, and
from 0.01% to 10% by weight of at least one gelling agent chosen from hydrophilic fumed silicas, hydrophobic fumed silicas, and hydrogenated block copolymers comprising at least one styrene block and at least one block chosen from ethylene/$C_3$-$C_4$ alkylene blocks, relative to the total weight of the paste; wherein said anhydrous paste has a water content less than 1% by weight relative to the total weight of the paste; and extemporaneously including in said composition at least one aqueous hydrogen peroxide composition.

23. A ready-to-use bleaching composition, comprising
(1) at least one anhydrous paste comprising
at least one peroxygenated salt,
at least one alkaline agent,
from 15% to 35% by weight of at least one polydecene of formula $C_{10n}H_{[(20n)+2]}$, wherein n ranges from 3 to 9, relative to the total weight of the paste, and
from 0.01% to 10% by weight of at least one gelling agent chosen from hydrophilic fumed silicas, hydrophobic fumed silicas and diblock, triblock, multiblock and radial-block copolymers comprising at least one segment of styrene monomers and at least one segment of monomers chosen from thermoplastic monomers and comonomers, relative to the total weight of the paste; and
(2) at least one aqueous hydrogen peroxide composition;
wherein the at least one anhydrous paste is mixed with the at least one aqueous hydrogen peroxide composition immediately before use.

24. A ready-to-use bleaching composition, comprising
(1) at least one anhydrous paste comprising:
- from 10% to 70% by weight of at least one peroxygenated salt chosen from sodium persulphate and potassium persulphate, relative to the total weight of the paste,
- from 0.01% to 40% by weight of at least one alkaline agent, relative to the total weight of the paste,
- from 15% to 35% by weight of at least one polydecene of formula $C_{10n}H_{[(20n)+2]}$, wherein n ranges from 3 to 9, relative to the total weight of the paste, and
- from 0.01% to 10% by weight of at least one gelling agent chosen from hydrophilic fumed silicas, hydrophobic fumed silicas and hydrogenated block copolymers comprising at least one styrene block and at least one block chosen from ethylene/$C_3$-$C_4$ alkylene blocks, relative to the total weight of the paste; and (2) at least one aqueous hydrogen peroxide composition;
wherein the at least one anhydrous paste is mixed with the at least one aqueous hydrogen peroxide composition immediately before use.

25. A process for bleaching human keratin fibers, comprising:
mixing, immediately before use, at least one anhydrous paste comprising at least one peroxygenated salt, at least one alkaline agent, from 15% to 35% by weight of at least one polydecene of formula $C_{10n}H_{[(20n)+2]}$, wherein n ranges from 3 to 9, relative to the total weight of the paste, and from 0.01% to 10% by weight of at least one gelling agent chosen from hydrophilic fumed silicas, hydrophobic fumed silicas and diblock, triblock, multiblock and radial-block copolymers comprising at least one segment of styrene monomers and at least one segment of monomers chosen from thermoplastic monomers and comonomers, relative to the total weight of the paste with at least one aqueous hydrogen peroxide composition,
applying the mixture obtained to at least one area of the keratin fibers to be bleached,
leaving the mixture to act for a period of time that is sufficient to obtain a desired bleaching, and
removing the bleaching mixture by rinsing with water, optionally followed by washing with a shampoo and then drying.

26. The process according to claim 25, wherein the human keratin fibers are hair.

27. A process for bleaching human keratin fibers, comprising:
mixing, immediately before use, at least one anhydrous paste comprising from 10% to 70% by weight of at least one peroxygenated salt chosen from sodium persulphate and potassium persulphate, relative to the total weight of the paste, from 0.01% to 40% by weight of at least one alkaline agent, relative to the total weight of the paste, from 15% to 35% by weight of at least one polydecene of formula $C_{10n}H_{[(20n)+2]}$, wherein n ranges from 3 to 9, relative to the total weight of the paste, and from 0.01% to 10% by weight of at least one gelling agent chosen from hydrophilic fumed silicas, hydrophobic fumed silicas and hydrogenated block copolymers comprising at least one styrene block and at least one block chosen from ethylene/$C_3$-$C_4$ alkylene blocks, relative to the total weight of the paste with at least one aqueous hydrogen peroxide composition,
applying the mixture obtained to at least one area of the keratin fibers to be bleached,
leaving the mixture to act for a period of time that is sufficient to obtain a desired bleaching, and
removing the bleaching mixture by rinsing with water, optionally followed by washing with a shampoo and then drying.

28. The process according to claim 27, wherein the human keratin fibers are hair.

29. A multi-compartment device for bleaching human keratin fibers, comprising
at least one compartment comprising an anhydrous paste comprising at least one peroxygenated salt, at least one alkaline agent, from 15% to 35% by weight of at least one polydecene of formula $C_{10n}H_{[(20n)+2]}$, wherein n ranges from 3 to 9, relative to the total weight of the paste, and from 0.01% to 10% by weight of at least one gelling agent chosen from hydrophilic fumed silicas, hydrophobic fumed silicas and diblock, triblock, multiblock and radial-block copolymers comprising at least one segment of styrene monomers and at least one segment of monomers chosen from thermoplastic monomers and comonomers, relative to the total weight of the paste, and
at least one other compartment comprising an aqueous hydrogen peroxide composition.

30. The multi-compartment device according to claim 29, wherein the human keratin fibers are hair.

31. A multi-compartment device or for bleaching human keratin fibers, comprising
at least one compartment comprising an anhydrous paste comprising from 10% to 70% by weight of at least one peroxygenated salt chosen from sodium persulphate and potassium persulphate, relative to the total weight of the paste, from 0.01% to 40% by weight of at least one alkaline agent, relative to the total weight of the paste, from 15% to 35% by weight of at least one polydecene of formula $C_{10n}H_{[(20n)+2]}$, wherein n ranges from 3 to 9, relative to the total weight of the paste, and from 0.01% to 10% by weight of at least one gelling agent chosen from hydrophilic fumed silicas, hydrophobic fumed silicas and hydrogenated block copolymers comprising at least one styrene block and at least one block chosen from ethylene/$C_3$-$C_4$ alkylene blocks, relative to the total weight of the paste, and
at least one other compartment comprising an aqueous hydrogen peroxide composition.

32. The multi-compartment device according to claim 31, wherein the human keratin fibers are hair.

* * * * *